United States Patent
Al-Falahe

[11] Patent Number: 5,979,447
[45] Date of Patent: *Nov. 9, 1999

[54] OCCLUSIVE DRESSINGS

[76] Inventor: Najem Al-Falahe, Skvadronbacken 51, S-172 47 Sundbyberg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,126

[22] PCT Filed: May 10, 1995

[86] PCT No.: PCT/SE95/00514

§ 371 Date: Nov. 14, 1996

§ 102(e) Date: Nov. 14, 1996

[87] PCT Pub. No.: WO95/30408

PCT Pub. Date: Nov. 16, 1995

[30] Foreign Application Priority Data

May 10, 1994 [SE] Sweden ................................ 9401620

[51] Int. Cl.[6] ........................................................ A61F 6/02
[52] U.S. Cl. ........................... 128/842; 128/844; 128/918
[58] Field of Search ................................... 128/842, 844, 128/918; 604/347–353

[56] References Cited

U.S. PATENT DOCUMENTS

| 4,446,860 | 5/1984 | Gutnick | 128/844 |
| 4,795,425 | 1/1989 | Pugh | 128/844 |
| 4,829,991 | 5/1989 | Boeck | 128/844 |
| 4,840,188 | 6/1989 | Heidenfelder | 128/844 |
| 5,333,621 | 8/1994 | Denzer | 128/844 |

Primary Examiner—Michael A. Brown
Attorney, Agent, or Firm—Robert H. Kelly

[57] ABSTRACT

The present invention relates to an occlusive dressing selected from the group consisting of e.g. a condom, a pessary or a femidom comprising a local anaesthetic and optionally a penetration enhancing formulation for postponement of ejaculation, especially for the treatment of premature ejaculation (PME). The local anaesthetic is, in case the occlusive dressing is a condom, applied on the whole or substantially the whole inside of the occlusive dressing when the condom is in essentially unrolled condition. The product can also be used by partners, not suffering from PME but who simply want to have a longer sexual intercourse. The invention further comprises the use of local anaesthetic in the manufacturing of a means for postponement of ejaculation.

8 Claims, 2 Drawing Sheets

OCCLUSIVE DRESSINGS

FIELD OF THE INVENTION

The present invention relates to an occlusive dressing comprising a local anaesthetic, and the use of local anaesthetics in combination with occlusive dressings for the preparation of a product useful for postponement of male ejaculation. More specifically it relates to the use of local anaesthetics and occlusive dressings of the condom type for the preparation of a product useful in the treatment of premature ejaculation (PME).

The product can also be used by partners, not suffering from PME but who simply want to have a longer sexual intercourse, and the occlusive dressing also may be a pessary or a femidom (i.e. an occlusive dressing having the same effect as a condom, but designed to be worn in the vagina).

BACKGROUND OF THE INVENTION

The definition of the term "premature ejaculation" according to DSM-III-R is "a presistent or recurrent ejaculation with-minimal sexual stimulation before, upon or shortly after penetration and before the person wishes it".

To a man skilled in the art the terms "erectile dysfunction" and "premature ejaculation" are two entirely separate concepts based on different etiologies (see British Journal of Hospital Medicine, Vol 40, Dec. 1988, p. 428 och 434).

Studies have shown that PME is a widespread problem in sexual relationships. Indeed, mention is made of as much as 75 % of men ejaculating within 2 minutes after penetration, and an important number of men reaching climax even within 1 minute of coitus.

This situation may be the cause of psychological disturbances for the man suffering from PME, as well as for his female partner.

There is no reliable documentation identifying the etiology of PME, but different theoretical concepts exist. They relate the problem 1) hypersensitivity of the glans penis, resulting in excessive stimulation of the sexual center in the central nervous system, 2) anxiety, 3) destructive interactional patterns, 4) learning and conditioning from early sexual experiences, and 5) multi-factorial causes.

The presently existing methods of treating PME are on the one hand of a psychological or "technical" type, such as the "pause-squeeze" method (W. H. Masters and V. E. Johnson, Human Sexual Inadequacy, Little; Brown & Company, Boston, Mass., 1970) and on the other hand of the pharmacological type. Thus, a variety of pharmacological techniques have been reported to delay or block an ejaculatory response. While reporting variable success rates, studies have been largely uncontrolled. Apart from the use of systemic drugs such as antidepressants or beta blockers, with evident drawbacks resulting from the side effects of the pharmaceutical, one of the interventions has been to apply topical anaesthetic to the penis before the sexual intercourse (Schapiro, J. Urology, 50, 374–379, 1943. Aycock, J. Urology, 62, 361–362, 1949. Damrav, J. Urology, 89, 936–939, 1963).

However, the use of the local anaesthetic alone has in most instances given only mediocre improvments, prolonging the coitus with on the average less than 2 minutes.

U.S. Pat. No. 3 363 624 to Fishman discloses a medicated prophylactic device comprising, in combination, an elastic tubular sheet having an open proximal end and a closed distal end, and provided adjacent the inner surface of the distal end thereof with about 0,2 to 5 cc. of a readily water-dispersible desensitizing composition, containing about 0,5 to25 % by weight of a desentizing agent, the amount of said composition and the concentration of the desensitizing agent in said composition being effective for only temporarily desensitizing a body member inserted in said device. The protective sheath, when used on the male organ increases the period of active intercourse prior to spermatic emission. However, at column 3, lines 19–23 it is stated that "For use on the male organ, an amount of desensitizing composition only sufficient to coat the glans penis or head of the male organ need be applied to the inner surface of the sheath.

U.S. Pat. No. 4 840 188 to Heidenfelder discloses a condom for use by a male human during sexual intercourse comprising a phallic-shaped elastic sheath having a closed end and an open end, a local coating on the inside surface of said closed end, said local coating consisting essentially of a topical anesthetic for delaying ejaculation by said male human during sexual intercourse and a water-soluble base therfor, and a small colored bump on said sheath solely adjacent to said open end, said mark being visually distinct from the color of said sheath and visually indicating said inside surface on which said local coating is located. At column 1, lines 11–13 it is stated that: By "local coating" is meant a coating over only a limited area of the inner surface.

Thus, it is obvious that prior art dissuades from the use of anaesthetics on the whole or substantially the whole inside surface of the condom.

EP 0 266 968 relates to a diagnostic and therapeutic method for human erectile failure by administering a smooth muscle relaxant to the human penile arteries. The aim with the use of a condom is according to p. 4 lines 10–18 to control abuse of the drug.

WO 89/11853 discloses the use of local anaesthetic agents in the manufacture of preparations with wound healing effects especially for the treatment of leg ulcers.

Thus, the dressing or use as disclosed by the present application are not anticipated by known prior art.

It is generally admitted that the mechanism of action of topical anaesthetics consists of a blocking of the pain skin receptors and pain fibers, thus providing analgesia. The local anaesthetics may also block the tactile receptors and the nerve fibers that convey the tactile sensory input, which is important for ejaculation.

Many topical anaesthetics in use for local analgesia have existed on the market for a long period or time, e.g. the last 30 years. They have been used among others in procedures involving the male and female urethra and as anaesthetic lubricant for endotracheal intubation (oral or nasal). They accordingly have had time to be well studied and have rare skin and mucosal irritation (less than $1/1000$).

SUMMARY OF THE INVENTION

The object of the invention is to provide an improved product for the postponement of ejaculation especially treatment of PME. This product is achieved by the use of local anaesthetics in combination with an occlusive dressing, more specifically an occlusive dressing selected from the group consisting of a condom, a pessary or a femidom, preferably a condom.

The product can also be used by partners, not suffering from PME but who simply want to have a longer sexual intercourse, and the occlusive dressing also may be a pessary or a femidom (i.e. an occlusive dressing having the same effect as a condom, but designed to be worn in the vagina).

The objects as disclosed according to the invention are those as future defined in the claims.

DETAILED DESCRIPTION OF THE INVENTION

Figure 1:
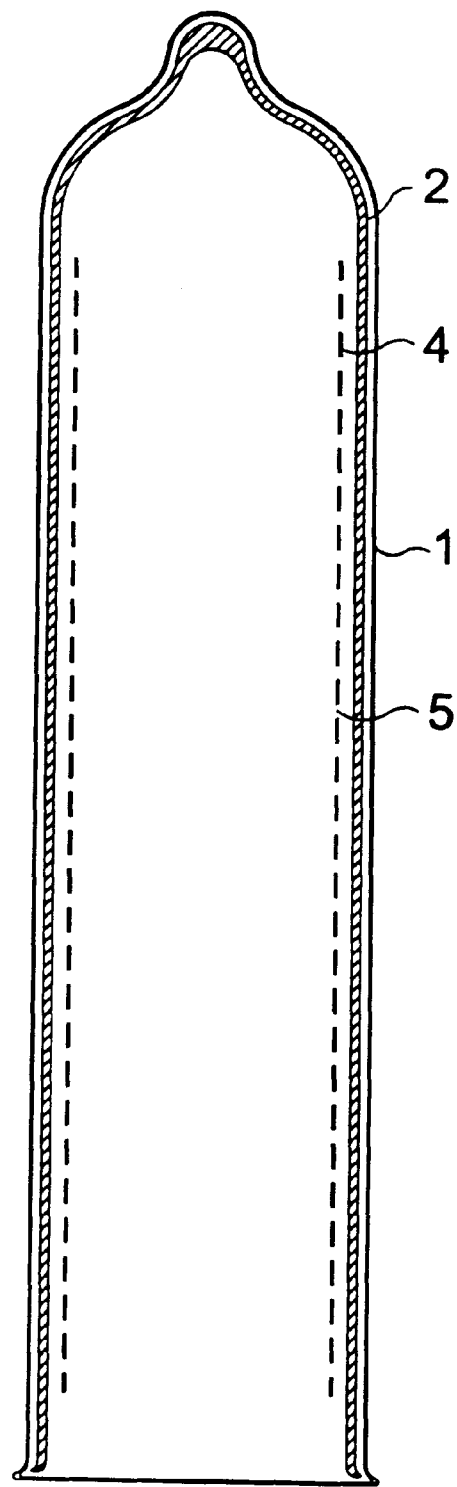

Local anaesthetics have the ability of abolishing the sensation at the site of application. They penetrate intact skin and the mucous membrane due to their pharmaceutical properties, or may be transported into the skin and underlying tissues by the use of iontophoresis, or by the addition of a penetration enhancing formulation (e.g. DMA or Azone®).

The formulation should contain at least one local anaesthetic agent, available now in use, in the form of its base or a pharmaceutically acceptable salt thereof, or a eutectic mixture of local anaesthetics or the aminoamide type (e.g. lidocaine, mepivacine, procaine, prilocaine, bupivacaine etc.).

The local anaesthetic(s) is (are) incorporated into a jelly, emulsion, cream, ointment, spray solution or film-forming formulation.

The local anaesthetic composition contains from 0,25% to 20% by weight of the local anaesthetic(s), preferably 2%–10%.

The local anaesthetic anaesthetics is (are) available commercially and examples of their pharmaceutical formulations are as follows:

Formulation 1: Ointment 5% (1 g)
Lidocaine 50 mg
propylene glycol
macrogol
aq. purif. qs
Formulation 2: Jelly 2% (1 ml)
Lidocaine hydrochloride 20 mg
chlorohexidine gluconate
metagin preservatives
propagin
propylene glycol
hydroxyethyl cellulose
aq. steril. qs The above formulations are only given as non limative examples, and while formulation 2 is preferred, any formulation containing one or more anaesthetics, optionally in the form of a physiologically acceptable salt, can be used for the purpose of the invention.

The preparation, if desired, can also contain various perfumes, colouring agents, and flavouring agents, e.g. fruit flavours. Any ingredients which are used must be skin compatible, inert towards the active ingredient, and of a nature and used in an amount which does not destabilize or upset the general consistency of the formulation.

The occlusive dressing preferably is of a latex material or a non-allergic material and of the condom type.

The local anaesthetic will be present inside the occlusive dressing either on its whole inside surface or on only part of it, in an amount of 0,5–3 ml, preferably 1–2 ml.

The occlusive dressing according to the invention for the postponement of ejaculation is e.g. a condom, a pessary or a femidom applied to which is a layer of a local anaesthetic The layer of local anaesthetics applied in a way permitting contact between the human penis and said layer of local anaesthetic. In the case the dressing is in the form of a condom, the whole inside surface or substantially the whole inside surface of the condom is provided with a layer of said anaestheticum.

The local anaestheticum is preferably present as a film on the inside surface of the occlusive dressing and may be provided with a penetration enhancing formulation.

The occlusive dressing according to the invention may consist of at least two layers, between two of which the local anaestheticum and optional penetration enhancing formulation are present as an intermedial layer, the outer being impermeable to the local anaestheticum and the inner permeable to the same.

The inner layer is provided with openings, preferable perforated to facilitate contact between local anaestheticum and penis.

To protect the outer layer and the partners from being contaminated from the local anaestheticum, the occlusive dressing may be provided with a protective layer covering and surrounding the occlusive dressing, especially the condom, in rolled as well as in unrolled condition. According to a preferred embodiment the protective layer is a sheet surrounding the condom, which sheet is sufficiently thin to permit the condom with its different layers to be rolled and packed and yet protected from contamination. The protective sheet shall remain around the condom when the condom is unrolled and applied to the penis it shall further, when the condom is applied, be easily removable be gripping an edge of the sheet and tear it off.

Figure 2:
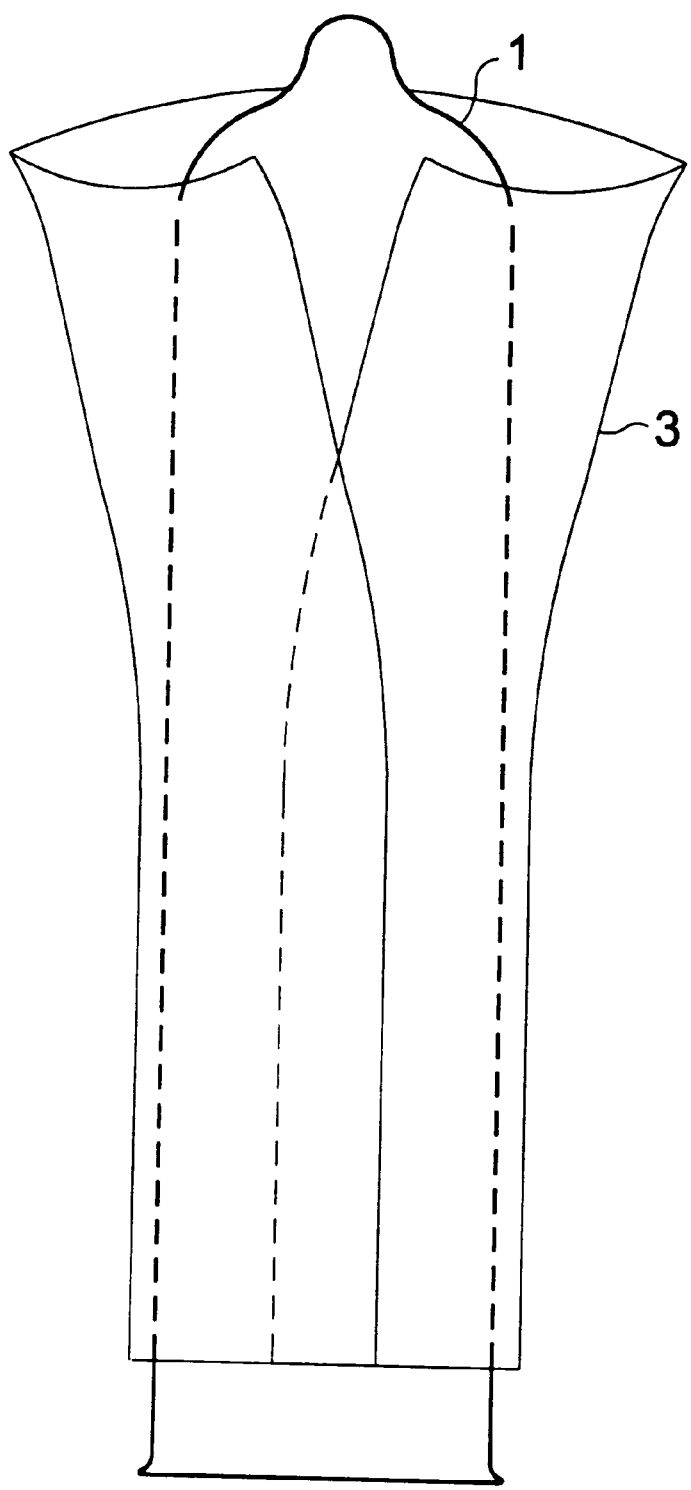

Thus, the sheet should be loosely applied around the condom and adhere only by gluing overlapping edges of the sheet (FIG. 2).

The outer layer is impermeable to the local anaestheticum when the occlusive dressing is double-layered, whereas the inner layer lets the local anaesthetic pass towards the skin when the occlusive dressing is in place. This inner layer can e.g. be of the same material as the outer layer, but transpersed with openings such as holes. It can also be any porous membrane or reticulous material, inert to the local anaesthetic.

To obtain the best effect with a condom, the condom containing the local anaesthetic should be worn over an appropriate time period, e.g. 3–10 minutes, before the intercourse or as soon as the penis is hard enough to keep the condom in place.

The invention comprises also the occlusive dressing provided with anaestheticum packed in a disposable package.

The invention will now be illustrated by way of non-limiting examples referring to the drawings wherein:

FIG. 1 represents a longitudinal sectional view of a condom 1 containing a film 2 of a local anaesthetic. The local anaeisthetic is present on the whole of the inner surface of the condom which optionally has a double-layered structure 4 having openings 5 as described herein above.

FIG. 2 represents a longitudinal view of a condom 1 surrounded by a protective overlapping sheet (3) which is easily removable by tearing. The local anaestheticum and optional inner layer are not shown.

TEST OF A PRODUCT ACCORDING TO THE INVENTION

A product according to the invention has been submitted to the following test wherein the use of a product according to the invention was compared to the use of the local anaesthetic alone and to that of the condom alone, respectively.

The test was performed on six subjects suffering from PME, aged from 23 to 37 years (average 26,3 years).

Each subject reported a total of three intercourses with an interval of 48–72 hours between each intercourse, using each one of the three different methods once, namely i) the condom only;

ii) the local anaesthetic only; and iii) a combination of the condom and the local anaesthetic covering substantially the whole inside of the condom.

The results of the test are reported in the following table.

TABLE I

Mean value of time duration between penetration and ejaculation in six subjects suffering from PME

| Condom only | Anaesthetic only | Combination of Condom and Anaesthetic |
|---|---|---|
| 0.26 min (0.16) | 1.42 min (0.53) | 3.5 min (1.26) |

Footnote: The value in brackets after each time duration value indicates the corresponding standard devaiation in minutes.

From the table it can be seen that whereas the use of the condom alone gives practically no delay of the time from penetration until ejaculation, the use of the anaesthetic alone results in a certain delay of the ejaculation, which however is considerably improved by the use of a combination of the condom and the anaesthetic.

In a further test, the combination product was tested in a subject, aged 21 years, who suffers from PME: he ejaculated before penetration as soon as the penis contacted the vulva A topical local anaesthetic (Xylocain gel 2%) was applied on the glans penis and partly on the shaft about 5 minutes before the sexual intercourse.

The time between penetration and ejaculation was delayed slightly but not drastically. He could penetrate and then ejaculated directly. The same effect was gained by applying the local anaesthetic on the penis before the sexual intercourse.

When combining the local anaesthetic application and condom, a surprising delay of the ejaculation was encountered. The subject could hold his ejaculation for more than 2 minutes after penetration, without any movement restriction.

The above examples show that a combination of anaesthetic and condom gives a clear synergistic effect, moreover it is handy to use one product instead of two products.

Further comparative tests were made on: (1) the use of only condom; (2) the use of a condom with the local anaestheticum at the distal end of the condom; (3) and the use of a condom with the whole of the inner surface covered by local anaestheticum. Three subjects at an age of 21, 24 and 27 respectively reported each a total of six intercourses with an interval of 48–72 hours between each intercourse, using each one of the three different methods twice. The results are given in table II.

TABLE II

Mean value of time duration between penetration and ejaculation in three subjects suffering from PME

| (1) | (2) | (3) |
|---|---|---|
| 0.52 min (0.18) | 1.24 min (0.32) | 4.27 min (1.31) |

Footnote: The value in brackets after each time duration value indicates the corresponding standard deviation in minutes.

Thus, table II shows a dramatic prolongation of the time of intercourse when a condom having the inner surface entirely covered with a local anaestheticum. The use of a condom having only the distal end covered with a local anaestheticum gave only about a duplicate of the value.

The present approach to treat PME is an easy one and can be used by single men, in contrast to most of the available methods, which are designed to treat PME in partners with a steady relationship. Moreover the invention encourages male and female to use condom. This encouragement has a positive effect on the prevention of sexually transmitted diseases. It has been shown that the penetration of medicine to skin can be affected physiologically by hydration of the corneated layer. Normally, the layer consists of 5–15 % of water. One effective way to reach water accumulation is to cover the application site with a plastic material, which is called a plastic occlusive. It has been demonstrated that the penetration of hydrocortisone increased ten times by this method (Apoteksbolaget, January 1983, 86 14-01, L äkemdelsformer och förpackning, page 57, Glukokortikoider i dermatologin, Hans Rosman SoS kommittéför 1 äkemedels-info, 4:1 1978). Thus, it seems likely that the synergistic effect of the local anaesthetic and the occlusive dressing having the whole inner surface or substantially the whole inner-surface covered with a local anaestheticum is a result of the hydration effect of the corneated layer.

Thus, the present invention gives the advantage of a convenient non-sticking occlusive dressing to be used for the postponement of ejaculation for men suffering from PME or as a means for partners who want to have a longer sexual intercourse.

I claim:

1. An occlusive dressing, when worn by a user for facilitating postponement of ejaculation, said occlusive dressing comprising:

an elongated sheath having a closed distal end and an open proximal end, said elongated sheath defining a tubular, inner surface extending between the open proximal end and the closed distal end; and a layer of local anaestheticum applied along all surface portions along at least a substantial portion of an entire length of the tubular inner surface of said elongated sheath, said layer of local anaestheticum forming a topical anaesthetic for anaesthesizing sensation at areas of user-contact along the at least substantial portion of the entire length of the tubular inner surface upon which said layer of local anaestheticum is applied, thereby to faciliitate the postponement of ejaculation by the user through the anaesthesizing sensation provided to the user by said layer of the local anaestheticum.

2. The occlusive dressing of claim 1 wherein said layer of local anaestheticum further comprises a penetration enhancing formulation.

3. The occlusive dressing of claim 1 wherein said layer comprises 0.5 to 3 ml. of local anaestheticum applied to the inner surface of said elongated sheath.

4. The occlusive dressing according of claim 1 wherein the local anaestheticum is selected from the group consisting of: a base, a pharmaceutically acceptable salt of a base, a eutectic mixture of the local anaesthetic, an aminoamide type mixture of the local anaesthetic (e.g. lidocaine, mepivacaine, procaine, prilocaine, bupivacine etc).

5. The occlusive dressing of claim 4 wherein said local anestheticum incorporates a preparation selected from the group consisting of: a jelly, emulsion, cream, ointment, spray solution or film-forming formulation, optionally also containing various perfumes, colouring agents and flavouring agents.

6. An occlusive dressing, when worn by a user for facilitating postponement of ejaculation, said occlusive dressing comprising:

an elongated sheath having a closed distal end and an open proximal end, said elongated sheath defining a tubular, inner surface extending between the open proximal end and the closed distal end;

a layer of a local anaestheticum applied along at least a substantial portion of the tubular inner surface of said elongated sheath, said layer of local anaestheticum forming a topical anaesthetic for anaesthesizing sensation at areas of user-contact along the at least substantial portion of the tubular inner surface upon which said layer of local anaestheticum is applied, thereby to facilitate the postponement of ejaculation by the user through the anaesthesizing sensation provided to the user by said layer of the local anaestheticum; and an inner-permeable membrane layer positioned within said elongated sheath, said inner-permeable membrane permeable to said layer of the local anaestheticum to provide the user-contact with said layer of the local anaestheticum.

7. The occlusive dressing of claim 6 wherein said inner-permeable membrane includes perforated openings extending therethrough to permit permeation of said local anaestheticum to the user.

8. An occlusive dressing, when worn by a user for facilitating postponement of ejaculation, said occlusive dressing comprising:

an elongated sheath having a closed distal end and an open proximal end, said elongated sheath defining a tubular, inner surface extending between the open proximal end and the closed distal end;

a layer of a local anaestheticum applied along at least a substantial portion of the tubular inner surface of said elongated sheath, said layer of local anaestheticum forming a topical anaesthetic for anaesthesizing sensation at areas of user-contact along the at least the substantial portion of the tubular inner surface upon which said layer of local anaestheticum is applied, thereby to facilitate the postponement of ejaculation by the user through the anaesthesizing sensation provided to the user by said layer of the local anaestheticum; and a removeable outer layer removably positioned about said elongated sheath, said outer layer positioned about said elongated sheath to prevent said layer of local anaestheticum from contacting with an outer surface of said elongated sheath when rolled into a rolled condition.

\* \* \* \* \*